(12) United States Patent
Hottinger et al.

(10) Patent No.: US 8,672,987 B2
(45) Date of Patent: *Mar. 18, 2014

(54) HANDPIECE WITH OPTICAL UNIT OF A SKIN PHOTOTREATMENT DEVICE

(75) Inventors: Christophe Hottinger, Paris (FR); Pascale Tannous, Paris (FR)

(73) Assignee: Dormed, Paris (FR)

( * ) Notice: Subject to any disclaimer, the term of this patent is extended or adjusted under 35 U.S.C. 154(b) by 115 days.

This patent is subject to a terminal disclaimer.

(21) Appl. No.: 13/063,448

(22) PCT Filed: Sep. 10, 2009

(86) PCT No.: PCT/FR2009/051700
§ 371 (c)(1),
(2), (4) Date: May 20, 2011

(87) PCT Pub. No.: WO2010/029258
PCT Pub. Date: Mar. 18, 2010

(65) Prior Publication Data
US 2011/0213447 A1    Sep. 1, 2011

(30) Foreign Application Priority Data

Sep. 12, 2008 (FR) ...................... 08 56152
Sep. 9, 2009 (FR) ...................... 09 56124

(51) Int. Cl.
*A61N 5/06* (2006.01)
(52) U.S. Cl.
USPC ............ 607/90; 607/88; 606/9; 606/13
(58) Field of Classification Search
USPC ............ 606/1, 9, 10, 13, 16–18, 20–23; 607/88–91
See application file for complete search history.

(56) References Cited

U.S. PATENT DOCUMENTS

| 5,344,418 | A  | * | 9/1994 | Ghaffari ............................ 606/9 |
| 5,830,208 | A  | * | 11/1998 | Muller .............................. 606/9 |
| 6,632,219 | B1 | * | 10/2003 | Baranov et al. .................... 606/9 |
| 6,758,845 | B1 | * | 7/2004 | Weckwerth et al. ............... 606/9 |
| 2007/0198004 | A1 | | 8/2007 | Altshuler |
| 2011/0238142 | A1 | * | 9/2011 | Hottinger et al. ............... 607/90 |

FOREIGN PATENT DOCUMENTS

| EP | 1535582 A | 6/2005 |
| WO | WO 03/043514 A | 5/2003 |
| WO | WO 2007/007167 A | 1/2007 |
| WO | WO 2008/012519 A | 1/2008 |
| WO | WO 2008/070747 A | 6/2008 |
| WO | WO 2008/088792 A | 7/2008 |
| WO | WO 2008/088795 A | 7/2008 |

* cited by examiner

*Primary Examiner* — Ahmed Farah
(74) *Attorney, Agent, or Firm* — Drinker Biddle & Reath, LLP

(57) ABSTRACT

Handpiece formed of a shell with a handgrip connected to a bundle of electrical power supply cables and of heat transfer fluid tubes and a head, accommodating a cartridge fitted with the controlled light source and with a light guide fed from the light source and the outlet surface of which constitutes the surface via which the light signal is emitted towards the surface of the skin that is to be treated. It comprises a housing, made in the shell, arriving under the emission surface of the cartridge and equipped with guide means and clip-fastening members. An interchangeable optical unit carrying the light guide is fitted removably into the housing. This optical unit has a casing accepting the light guide and equipped with guiding and clip-fastening surfaces to collaborate with the guide means and the retractable clip-fastening members belonging to the housing.

13 Claims, 4 Drawing Sheets

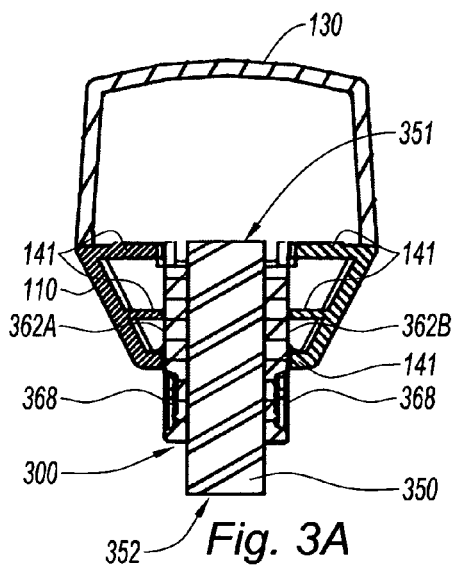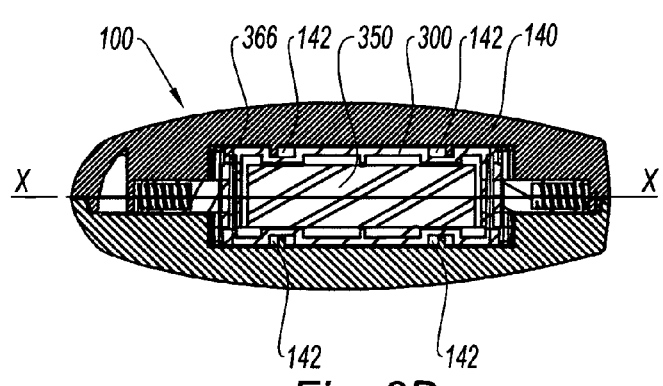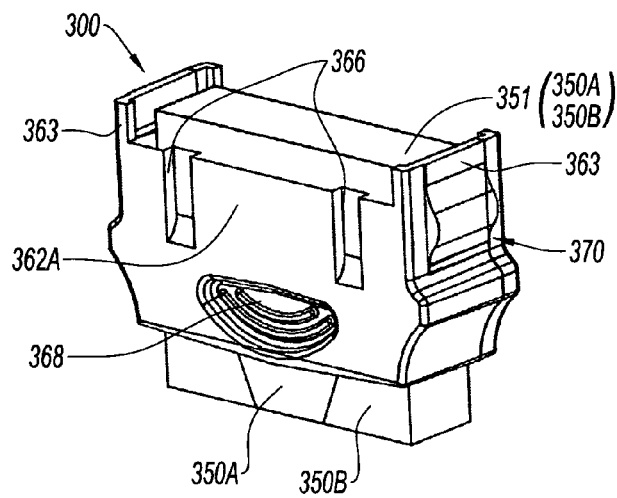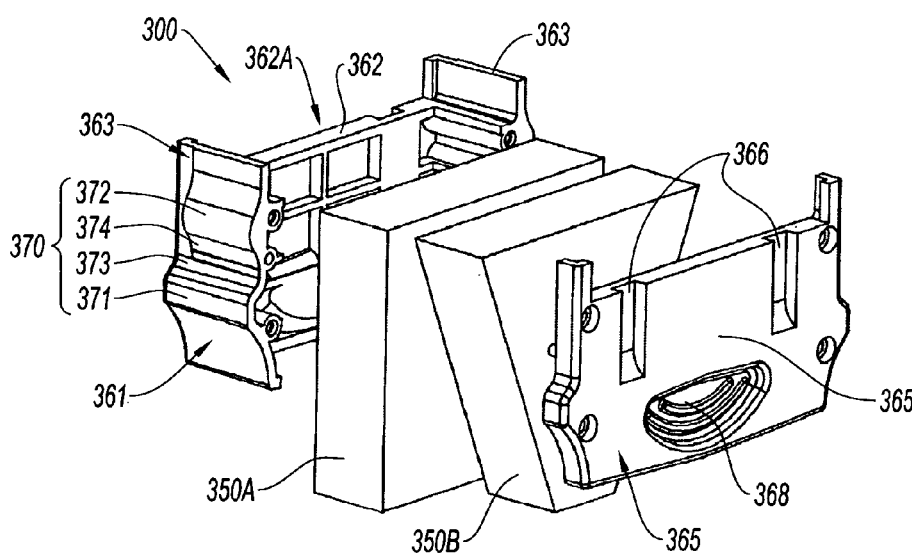

HANDPIECE WITH OPTICAL UNIT OF A SKIN PHOTOTREATMENT DEVICE

FIELD OF THE INVENTION

Figure 1:
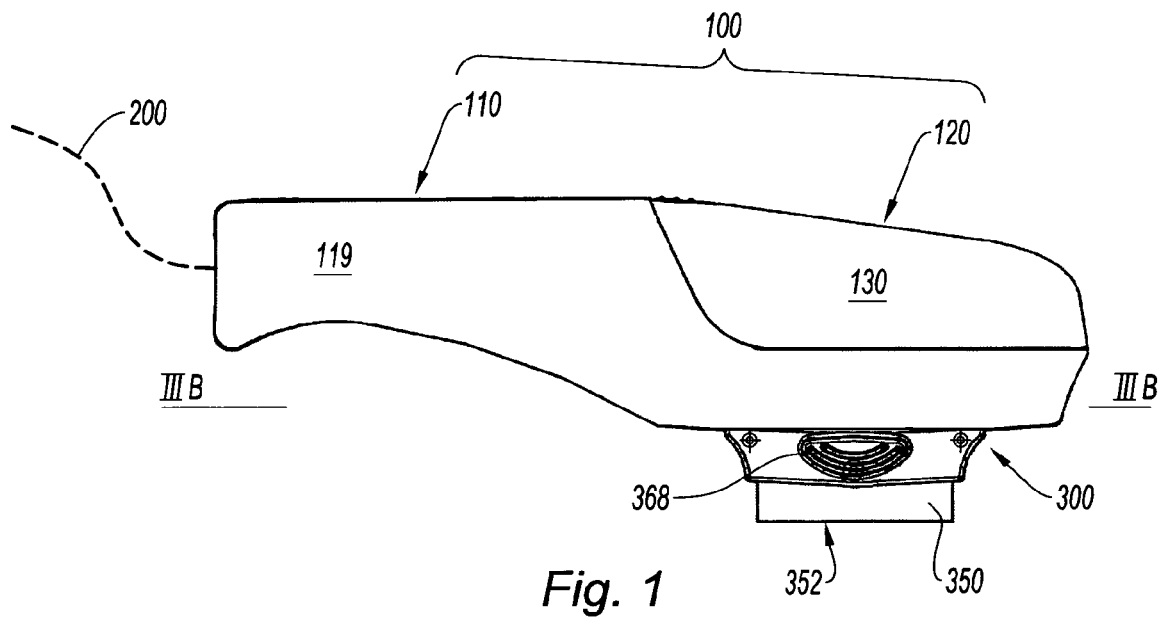

The present invention relates to a handpiece for a skin phototreatment device, which piece is formed by a shell having a handle, which is connected to a bundle of power supply cables and liquid coolant tubes, and a head, which receives a cartridge provided with the controlled light source and with a light guide fed by the light source and the outlet surface of which constitutes the emission surface of the light signal towards the surface of the skin to be treated.

PRIOR ART

Various forms of such skin phototreatment devices for carrying out cosmetic, medical or therapeutic treatments are already known. Such devices generally comprise a part constituting a stationary unit (although it may be mounted on wheels if required) connected to a handpiece which constitutes the element used for carrying out the treatment. The handpiece is brought close to the surface of the skin to be treated or is placed thereon in order to apply light signals thereto. The light signals can have very different physical characteristics according to their wavelength, the intensity of the beam, the pulse frequency of the beam and other parameters.

The light is emitted by a flashlamp housed in the handpiece. The lamp is fed in a controlled manner from a source located in the stationary unit of the device. A liquid cooling circuit is also provided. The circuit passes around the lamp light source and into a heat exchanger in the stationary unit, the fluid being circulated by a pump.

According to document WO2007/007167 there exists a flashlamp cartridge a version of which (FIG. 3) comprises an optical unit integral with the cartridge.

According to document EP 1 535 582 there is known a handpiece which is composed essentially of two parts, the case of the handpiece and the electronic and optical part constituted by a module which is slipped into the handpiece and thus fixed.

Replacement of the cartridge requires the removal of that overall piece and then the dismantling of the cartridge, the fitting of a new cartridge and finally the replacement of the casing in the opening of the handpiece. This known solution has the disadvantage of being relatively complex, and only a specialist will be able to remove the removable part of the handpiece and then open it in order to remove the cartridge therefrom and replace it if necessary.

In order to change the optical system, it is necessary to dismantle the entire cartridge, fit the new optical system and then reintegrate the whole into the handle of the handpiece.

OBJECT OF THE INVENTION

It is an object of the present invention to develop a handpiece for a skin phototreatment device which allows the handpiece to be adapted in a simple manner to different treatments that are to be carried out in order to concentrate, filter or emit the most appropriate light beam for the treatment without requiring considerable modification of the handpiece and especially allowing an operator to carry out such modifications of the handpiece in a particularly simple manner.

DESCRIPTION AND ADVANTAGES OF THE INVENTION

To that end, the present invention relates to a handpiece of the type defined above, characterised in that it comprises an open housing which is formed in the shell and extends to beneath the emission surface of the cartridge and which is provided with guide means and clip-fit elements, an interchangeable optical unit which carries the light guide and is engaged in a removable manner in the housing, the optical unit having a casing which receives the light guide and is provided with guide and clip-fit surfaces for cooperation with the guide means and the retractable clip-fit elements of the housing.

This handpiece with a removable optical unit allows the handpiece to be altered very quickly as a function of the treatment to be carried out. For the alteration, the optical unit simply has to be removed and replaced with an optical unit whose optical characteristics correspond to the treatment to be carried out. This allows different treatments to be alternated under good conditions and without losing time. No action on the handpiece itself is necessary; the handpiece does not have to be opened, connected or disconnected. The device is simply inactive so that the light source is not supplied with power.

That security can further be obtained with the aid of a sensor which detects the presence of an optical unit in the housing of the handpiece. In the absence of an optical unit, the sensor transmits a signal to the device, which thus blocks the operation of the light source in order to avoid possible dazzling or ocular injury.

When the work is complete, the optical unit can also be removed for storage, so as to protect it, and replaced with a blind optical unit, that is to say a cover which has the shape of the casing of the optical unit so as to be placed in the housing of the handpiece, to close the handpiece and prevent the penetration of dust or, possibly, accidental damage to the cartridge.

The casing of the cover can advantageously comprise an undercut at the location of the optical unit detector so that, even though it is placed in the housing of the optical unit, the casing does not allow operation of the light source.

According to another advantageous feature, the clip-fit elements are constituted by spring-mounted stops in the form of pistons, the head of which protrudes from the guide surface of the housing, and the casing of the optical unit comprises guide surfaces provided with a hollow forming a ramp for receiving the head of the piston of the associated clip-fit element.

These means are particularly simple and reliable to use. No particular effort is required to remove or insert the optical unit owing to the surfaces forming ramps which cooperate with the clip-fit elements. The means are very reliable and permit a large number of operating cycles.

According to another advantageous feature, the casing is constituted by an element of parallelepipedal shape, of generally rectangular cross-section, which is composed of a first part having a base and two sides and of a second part in the form of a cover, which parts constitute between them a cavity which is open on two sides for receiving the light guide, the two parts being fixed to one another in order to secure the light guide, and the sides forming the guide and clip-fit surfaces.

This form of the casing allows different forms of light guide to be received without having to prepare the shape of the casing in order to adapt it to the removable fitting of the optical unit in the shell of the handpiece.

According to another advantageous feature, the casing comprises grooves which are formed in the large sides to cooperate with homologous guide ribs of the housing of the shell.

According to another advantageous feature, in its surface which protrudes from the housing of the shell when the optical unit is in place therein, the casing comprises grip recesses on two large faces.

The removable optical unit according to the invention preferably comprises a light guide of quartz glass or sapphire glass. It may or may not provide optical filtration in order to sample the light spectrum as a function of the desired applications.

According to another feature, the optical unit is provided with a system for cooling the light guide using, for example, the Peltier effect.

According to an advantageous feature, the optical unit comprises an interface plate which is applied to the inlet face of the light guide and has optical characteristics for the transmission of light between the light source of the cartridge and the light guide.

The interface plate allows the light guide of the optical unit to be completed and the optical characteristics of the combination that it forms with the light guide to be provided so that the same light guide can be used to obtain different optical characteristics by virtue of different interface plates. The interface plates can have a treated face or can be mass-coloured in order to constitute an optical filter corresponding to a specific wavelength. The filtered light will be more or less precise according to whether a plate provided with a filtering coating or a mass-coloured plate is used.

The plate provided with the filtering coating is advantageously turned with its coated face against the light guide so that there is no risk of the coating being touched and suffering a chemical attack under the effect of contact with a finger of the operator.

Moreover, the production of the light guide in the form of an optically neutral element without any filtering effect considerably facilitates the production of the optical unit and inventory management because, for the different filtering characteristics, it will simply be necessary to modify the interface plate. This modification is all the more simple because the interface plate is slipped into the two grooves in the casing of the optical unit.

The interface plate also provides mechanical protection for the light inlet face of the light guide to which it is applied.

Finally, the plate has a mechanical function of securing the light guide in the casing because the light guide will be unable to escape from the casing in the direction of the interface plate.

This avoids the need to secure the light guide in the casing by adhesive dots.

Therefore, not only is an additional operation avoided; attack of the two faces of the optical unit by the adhesive, which modifies the interface in that region and promotes the emission of light rays through the faces of the light guide that are covered with adhesive, is also avoided. This reduces the optical efficiency of the light guide and causes heating of the side faces of the light guide and of the elements in contact therewith. By eliminating the adhesive dots, that source of light loss is eliminated.

According to another advantageous feature, the optical unit has a casing, the first part of which comprises a housing which receives the optical guide and, above the housing, two grooves in the small sides which receive the interface plate.

This embodiment is particularly valuable for replacing or changing the interface plate because it is simply necessary to remove the cover, which is generally screwed on, in order to be able to remove the plate and replace it with a new plate or a plate having different optical characteristics from the previous plate.

According to another advantageous feature, the casing of the optical unit comprises guide surfaces which are provided with a hollow forming a ramp and are preceded in the direction of engagement of the optical unit in its housing in the shell by two projections, the first of which serves to position the optical unit in the entry to the housing, and the second projection delimits the hollow receiving the head of the piston of each of the clip-fit elements.

This form of the two small sides of the casing of the optical unit facilitates the precise engagement of the optical unit in its housing in the handpiece in order to position the optical unit correctly relative to the cartridge housing the discharge lamp which generates the light signal to be transmitted. By virtue of this form, air interfaces between the window of the cartridge and the interface plate and between the interface plate and the inlet face of the light guide are avoided.

Furthermore, the surface of the interface plate is advantageously larger than that of the inlet face of the light guide so that the plate protrudes greatly from the inlet face on both sides so as to cover and extend beyond the window of the cartridge so that the interface plate always rests on the window with planar contact, the operation being facilitated by the shape of the guide surfaces of the optical unit.

According to another advantageous feature, the optical unit comprises, on the two faces of the light guide, a reflector in the form of a metal plate which is applied to each large face of the light guide in order to protect the casing from overheating.

The metal plates fitted to each large face of the light guide constitute an additional means for preventing light from being emitted via the large faces, which emission is inevitable whatever the mirror finish of the faces of the light guide. The casing of the optical unit is thus protected from local overheating.

DRAWINGS

Figure 2:
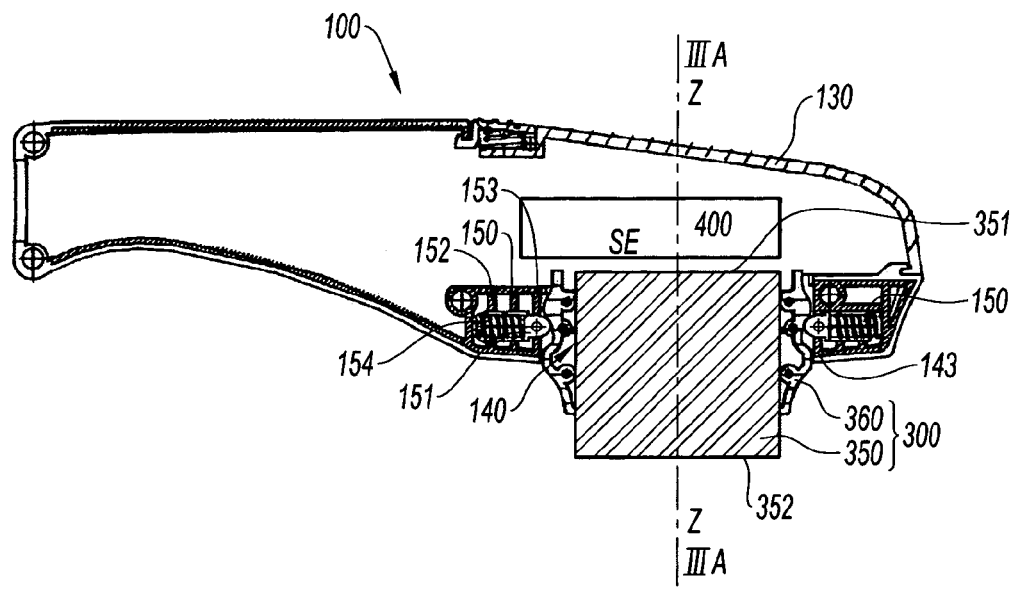
Figure 6:
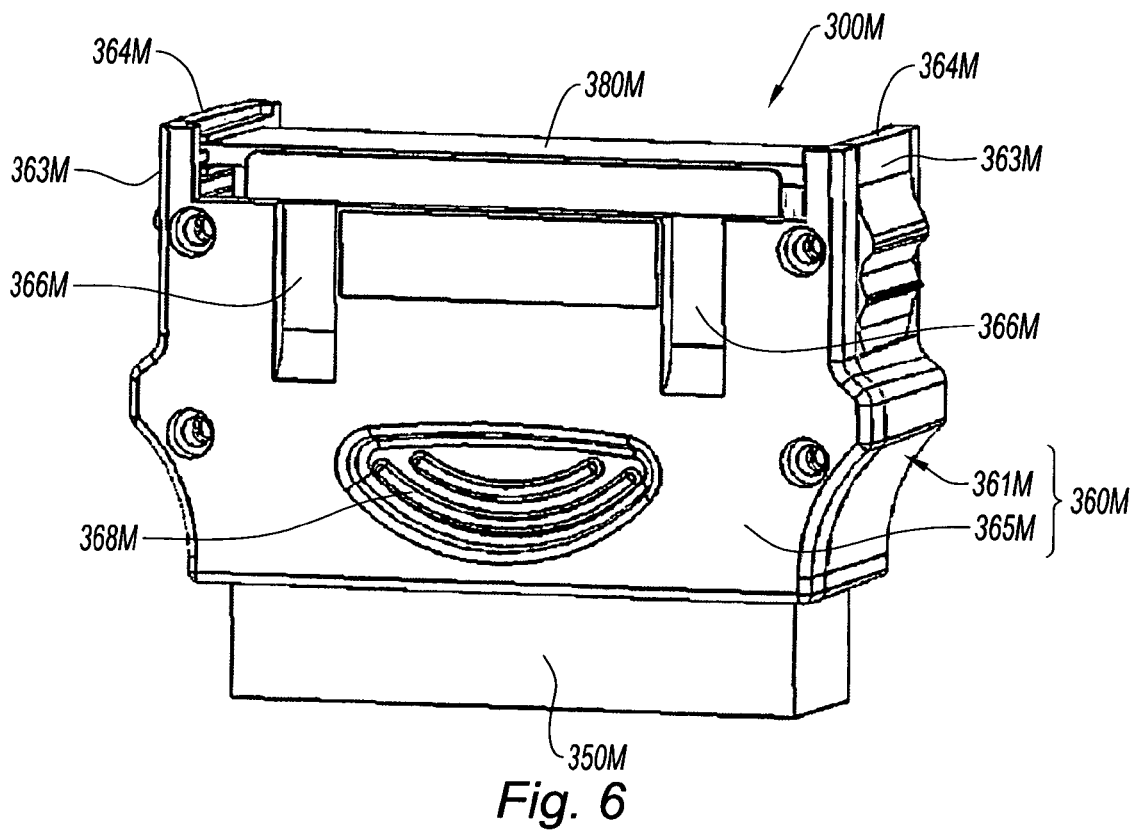
Figure 7:
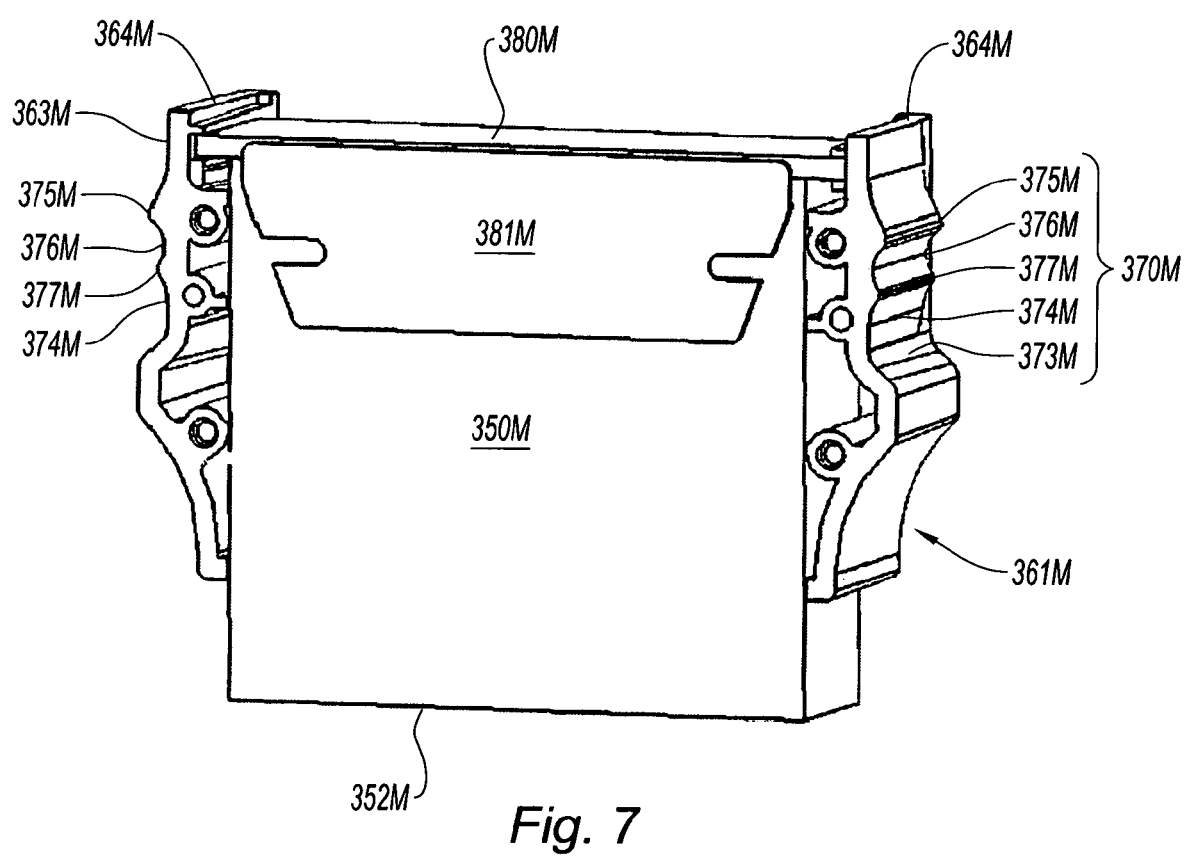
Figure 8:
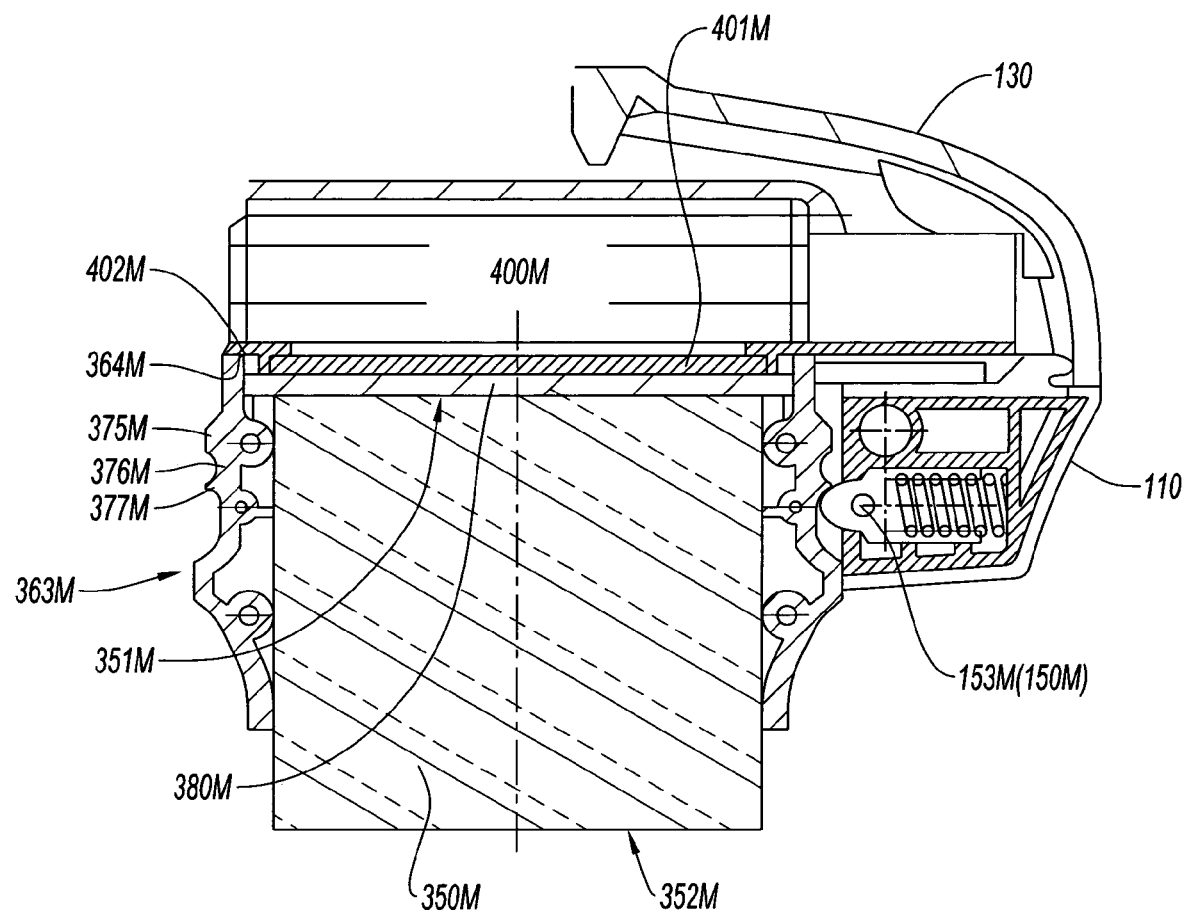

The present invention will be described in greater detail hereinbelow with the aid of embodiments of a handpiece having a removable and interchangeable optical unit which are shown diagrammatically in the accompanying drawings, in which:

FIG. 1 is a side view of a first embodiment of the handpiece according to the invention, FIG. 2 is a longitudinal sectional view through the midplane of the handpiece of FIG. 1, FIG. 3A is a section according to plane IIIA IIIA of FIG. 2, FIG. 3B is a section according to plane IIIB IIIB of FIG. 1, FIG. 4 is a perspective view of an optical unit for the handpiece of FIG. 1, FIG. 5 is an exploded view of the optical unit of FIG. 4, FIG. 6 is a perspective view of a variant of an optical unit according to the invention, FIG. 7 is a perspective view corresponding to FIG. 6 but in which the cover of the casing of the optical unit has been removed, FIG. 8 is a section of part of the handpiece and of the optical unit.

DESCRIPTION OF AN EMBODIMENT OF THE INVENTION

According to FIG. 1, the invention relates to a handpiece for a cosmetic, medical/therapeutic skin phototreatment device. The handpiece 100 is connected to the device proper (not shown) by a bundle of cables and of pipes 200 emerging from the end of the shell 110; the handpiece forms a handle 110 and a head 120 housing a cartridge with a controlled light source (not shown), which provides the light signals for treatment. The light source is in contact with a removable and interchangeable optical unit 300 carrying a light guide 350, for example of prismatic shape, whose face 351 (FIG. 2) on the inside of the shell 110 constitutes the inlet for the light signals emitted by the light source, and whose face 352 which is visible on the outside constitutes the emission face of the light signals; that face is directed towards the skin surface to be treated.

The sectional views of FIGS. 2 and 3 show the structure of the handpiece 100 for the parts limited to those relating to the present invention.

The shell 110 is constituted by the assembly of separately moulded parts 110a, b of plastics material and a removable cap 130 allowing access to the cartridge 400.

According to FIGS. 2, 3A, 3B, beneath the emission surface SE of the cartridge, the shell 110 has a housing 140 which opens to the outside of the shell and receives the optical unit 300; when viewed from above (horizontal section), the optical unit 300 has a substantially rectangular shape (FIG. 3B), the large length of which is directed in the longitudinal axis XX (called the horizontal axis) of the handpiece. The housing 140 is delimited on its large sides by horizontal ribs 131 (FIG. 3A) and guides 142 (FIG. 3B) oriented in the axis ZZ (called the vertical axis) of the housing, perpendicular to the axis XX; the small sides have guide surfaces 143 and at least one, and preferably two, clip-fit elements 150.

The ribs 142 (FIG. 3B) project into the housing 140 in order to cooperate with grooves 366 in the casing 360 of the optical unit 300. The guide surfaces 143 on the small sides are two planar surfaces, which are likewise parallel to the axis ZZ, from which the rounded head 153 of the piston 151 of each clip-fit element 150 protrudes. The pistons 151 slide in transverse housings 152 (direction XX of the shell 110) and their rounded head 153, which is optionally constituted by a bead, is pushed by a spring 154 so that it protrudes from the guide surface 143 or is retracted in the housing 152 in order to permit the passage of the relief portions of the small sides 363 of the casing 360 of the optical unit 300.

The optical unit 300 (FIGS. 4 and 5) is constituted by the casing 360 which receives the light guide 350. The light guide 350 is an element of a transparent material having the desired optical characteristics, for example of quartz. The light guide 350 has a parallelepipedal or prismatic shape with an inlet surface 351 and an outlet surface 352 for the light signal. The inlet surface 351 is intended to rest on the window of the cartridge 400 housing the light source, and the outlet surface 352 is the surface by which the light signal is directed towards the surface of the skin to be treated.

The casing 360 is formed by a first part 361 composed of a rectangular base 362 bordered by two opposite small sides 363 (the other two sides at the top and bottom being open), and by a second part 365 in the form of a cover fixed to the sides 363 of the first part and delimiting the open housing in which the light guide 350 is placed and secured. The light guide 350 has a parallelepipedal (350A) or prismatic (350B) shape or any other shape necessary for phototreatment. The light guides 350 differ in their geometric and optical characteristics. Preferably, the light guides have an external shape which allows them to be inserted into the same type of casing 360 in order to simplify manufacture. The light guides 350 are fitted integrally in the casing 360 to constitute an optical unit 300 which can be removed from the handpiece so as to be interchangeable as a function of the application.

The two large outside faces 362A, 365A of the casing 360 are identical. They each comprise two longitudinal guide grooves 366 in the direction ZZ in their upper zone for cooperation with the ribs 142 of the housing 140; in their lower portion, protruding from the shell 110 when the optical unit 300 is in position, they comprise a grip recess 368 equipped with ribs or anti-slide elements, allowing the optical unit 300 to be removed from its housing 140 in the shell 110 without touching the light guide 350 and, especially, its two inlet and outlet surfaces 351, 352. The grip recesses 368 constitute grip means which are used naturally; they allow an optical unit 300 to be removed and inserted by clipping it into its housing with one hand.

The inside face 362B of the large side 362 and that 365B of the cover 365 are ribbed so that they are rigid and hold the light guide 350.

The small sides 363 of the casing 360 are provided with surfaces 370 which define a clip-fit recess having a ramp for cooperation with the two piston heads 153 which face one another in the housing 140.

More precisely, the two opposite surfaces 370 are each composed of two projections 371, 372 which are separated by a dished portion 373 in such a manner as to form a ramp 374 which is inclined so that the piston head 153 on each side not only clips the optical unit 300 in the housing 140 but also presses against the upwardly facing ramp 374, providing an upward thrust component in the direction of the axis ZZ for applying the optical unit 300 against the upper stop surface formed by the window of the cartridge 400 of the light source.

It is also possible to produce a "blind optical unit" which forms a cover but does not have a light guide and which is engaged in the housing 140 after the optical unit equipped with its optical guide has been removed. In that manner, the housing 140 is closed while avoiding damage to the surface of the light guide during movement, maintenance work carried out in the premises or other situations of that type. The optical unit can be stored with the other optical units intended for each type of treatment.

FIGS. 6 to 9 show another embodiment of the optical unit which facilitates its production, its diversification and its insertion in its housing in the casing.

For the description of this variant, the same reference numerals will be used as for the first embodiment, with the addition of the suffix M to denote the elements that are identical with or have an analogous function to that of the first embodiment.

The description given below will be limited only to the differences, and common elements will not be described again for identical reference numerals, with the added suffix M.

According to FIG. 6, the removable optical unit 300M is composed of a casing 360M which houses a light guide 350M surmounted by an interface plate 380M applied directly to the inlet face 351M of the light guide 350. The interface plate 380M is itself to be applied as tightly as possible to the outside face of the pane of the window 401 of the cartridge 400 of the light source.

The casing 360M is composed of a first part 361M having a flat base 362M, which is optionally ribbed on the inside and is bordered by two small sides 363M serving as guide and clip-fit surfaces for the optical unit 300M in the housing of the handpiece. The first part 361M accordingly has a U-shaped cross-section, open at the top and at the bottom. The depth of this part is adapted to the thickness of the light guide 350 so that the second, flat part 365M, whose shape is adapted to the contour defined by the edges of the small sides 363M, forms a cover which closes the casing 360M while leaving the top and the bottom free.

The small sides 363M protrude from the large side and from the cover to form a groove 369M receiving the edge of the small side of the interface plate 380M. The groove is open on the cover side and closed on the base side. The two parallel grooves 369M are sufficiently remote from the sides of the light guide 360M that the interface plate 380M that they hold extends beyond the two small sides of the light guide 350M.

The interface plate 380M slides freely in the two grooves 369M for replacement by a different interface plate. The interface plate 380M, like the light guide 350M, is held in place in the casing by the cover 365M. A bearing and stop surface 364M defines precisely the position of the casing 360M and therefore that of the optical unit 300M surmounted by the interface plate 380M. The excess height of the two small sides 363M is fixed as a function of the space available around the window 401M of the cartridge 400 (see FIG. 8).

If the engagement movement of the casing 360M is not rigorous and the upper face of the plate 380M is inclined relative to the window 401M, there will be no risk of punctual or linear contact with the window since the forwardmost bearing surface 364A of one of the two sides 363M will first come into abutment against the set-back contour 402M of the window 401M and then the casing 360M will tilt so that the interface plate 380M will be applied flat to the window 401M. This avoids any risk of damage to the window 401M and/or the interface plate 380M.

The optical system constituted by the light guide 350M and the interface plate 380M allows multiple optical filtering characteristics to be obtained in a very simple manner. The light guide 350M is preferably an element of quartz without particular optical filtering characteristics, with only a light inlet face 351M and a light outlet face 352M and side faces having a mirror finish so that the light guide function is as good as possible.

The light guide 350M can have the shape of a rectangular parallelepiped or a truncated pyramid according to the distribution to be given to the light flux leaving the light guide.

The filter effect is advantageously provided by the interface plate 380M, which is a simple rectangular plate one face of which, preferably the face facing the light guide, has the filtering coating or is mass-coloured, according to the more or less precise filtering effect. The coating or mass-colouring are a function of the desired wavelength. The filtering coating is obtained by vapour deposition.

The process of metal vapour deposition is derived from thin-layer technology. The coating(s) can be deposited directly on the inlet face of the light guide in the first embodiment and, preferably in the present variant, on the interface plate.

Production of the optical system in the form of a neutral light guide and an interface plate also allows other light filtering techniques to be applied easily in order to limit the light to a specific wavelength using a mass-plate, which is certainly possible but very expensive in the case of a light guide.

The filtering coating applied to the face of the interface plate 380M that faces the light guide 350M will automatically be protected against any physical contact such as the touch of the handler's fingers. Because only the plate 380M has the required filtering characteristics, manufacture of the optical units and their adaptation to the particular optical filter to be produced are facilitated. This is effected simply by choosing the interface plate, the light guide 350M being the same for all the applications.

According to FIG. 7, which shows the casing 360M without the cover, the large face of the light guide 350M is covered in its upper portion by a reflective metal plate 381M, supplementing the effect of the reflective surface (mirror finish) of the face of the light guide in order to protect the cover 365M from the light radiation, which can be intense and pass through the dioptre of the face of the light guide 350M. The metal plate 381M is simply held in place by the pressure of the cover 365M. An identical plate is provided on the other large side of the light guide under the same conditions as those described above.

FIG. 7 also shows the profile of the two small sides 363M and their linear contact with the light guide 350M. The light guide is held in its housing by clamping at the sides and securing at the top by the interface plate 380M. In order to prevent any sliding movement of the light guide, its shape can be slightly trapezoidal, the large side being the side facing the interface plate 380M, which will secure it.

The small sides 363M of this variant of the optical unit 300M have a split projection 375M-377M which is of smaller height relative to the projection 372 of the first embodiment. The two projections form between them a dished portion 376M so as to create a haptic effect allowing the operator who fits the optical unit in the housing to detect the first projection 375M and accordingly the correct position for introduction of the casing. Then, it is able to pass the double projection 375M (one projection on each side), which is of small height and therefore offers low resistance to the introduction, which avoids excessive pressure on the unit 300M which might displace it. Then, after gently passing through the intermediate dished portion 376M and the second projection 377M, the optical unit is correctly positioned by the head 153M of the pistons 151M on the ramp 374M or beyond it in the dished portion 373M.

If, as shown in FIG. 8, the geometry of the small sides 363M and that of the position of the pistons 151M is defined so that the head 153M of the pistons 151M rests on the ramp 374M, there is thus created a longitudinal thrust component which acts on the optical unit 300M in order to apply it in its housing against the window 401M of the cartridge 400M.

FIG. 8 also shows the abutment of the bearing surfaces 374M of the small sides 373M against the bottom of the contour 402M of the window 401M, as well as the tight application of the interface plate 380M against the window 401M and against the inlet face 351M of the light guide 350M.

NOMENCLATURE 100 handpiece
110 shell
110a, b parts of the shell
119 handle
120 head
130 cap
140 housing of the optical unit
141 ribs
142 guide
143 guide surface
150, 151M clip-fit element
151 piston
152 transverse housing
153, 153M piston head
154 spring
200 bundle of cables and pipes
300 removable optical unit
350, 350M light guide
350A parallelepipedal shape
350B prismatic shape
351, 351M inlet face
352, 352M outlet face
360, 360M casing of the optical unit 361, 361M first part
362 rectangular base
362A, B large outside faces
363, 363M small side
364M bearing surface
365, 365M second part
365A large outside face
365B inside face of the cover 365
366, 366M longitudinal guide grooves
368, 368M grip recess
369M groove
370 surface
371, 372 projections
373, 373M dished portion
374, 374M ramp
375M projection
376M dished portion
377M projection
380M interface plate
381M metal plate
400M cartridge
401M window
402M set-back contour

The invention claimed is:

1. Handpiece for a skin phototreatment device, which piece is formed by a shell having a handle, which is connected to a bundle of power supply cables and liquid coolant tubes, and a head, which receives a cartridge provided with a controlled light source and with a light guide fed by the light source, the light guide having an outlet surface which constitutes an emission surface of light towards the surface of skin to be treated, characterised in that the handpiece comprises
an open housing defined by the shell and located below the cartridge and which is provided with guide means including a guide surface and retractable clip-fit elements, and
an interchangeable optical unit which carries the light guide and is engaged in a removable manner in the housing, the interchangeable optical unit having a casing which receives the light guide and is provided with guide and clip-fit surfaces for cooperation with the guide means and the retractable clip-fit elements of the housing for releasably receiving the interchangeable optical unit in the housing.

2. Handpiece according to claim 1, characterised in that the clip-fit elements are constituted by spring-mounted stops in the form of a piston, having a head which protrudes from the guide surface of the housing, and the casing of the optical unit comprises guide surfaces provided with a hollow forming a ramp for receiving the head of the piston of an associated clip-fit element.

3. Handpiece according to claim 2, characterised in that the easing of the optical unit comprises guide surfaces which are provided with a hollow forming a ramp and are preceded in the direction of engagement of the optical unit in the housing in the shell by two projections, the first of which serves to position the optical unit in the entry to the housing, and the second of which delimits the hollow receiving the head of the piston of each of the clip-fit elements.

4. Handpiece according to claim 1, characterised in that the casing of the optical unit is constituted by a light guide retaining element of parallelepipedal shape, of generally rectangular cross-section, which is composed of a first part having a base and two sides and of a second part in the form of a cover in mating engagement with the first part, which parts constitute between them a cavity which is open on two sides for receiving the light guide, the two parts being fixed to one another in order to secure the light guide in the cavity, the two sides defining the guide and clip-fit surfaces.

5. Handpiece according to claim 4, characterised in that the casing comprises grooves which are formed in the sides of the light guide retaining element to cooperate with corresponding guide ribs of the housing of the shell.

6. Handpiece according to claim 4, characterised in that a portion of the casing protrudes from the housing and is provided with grip recesses on the base and the cover of the light guide retaining element.

7. Handpiece according to claim 1, characterised in that the optical unit is provided with a system for cooling the light guide.

8. Handpiece according to claim 1, characterised in that the handpiece further comprises a blind optical unit for placing in the housing of the handpiece for closing the latter and preventing penetration of dust.

9. Handpiece according to claim 1, characterised in that the optical unit comprises an interface plate which is applied to an inlet surface of the light guide and has optical characteristics to facilitate transmission of light between the light source of the cartridge and the light guide.

10. Handpiece according to claim 9, characterised in that the interface plate includes one of a treated surface, an optical filter, and a mass-coloured plate that forms an optical filter.

11. Handpiece according to claim 9, characterised in that the casing of the optical unit comprises a housing which receives the light guide and above the light guide, includes two grooves in the casing which receive the interface plate.

12. Handpiece according to claim 1, characterised in that the optical unit comprises, on both light inlet and light outlet surfaces of the light guide, a reflector in the form of a metal plate which is applied to each surface of the light guide in order to protect the casing from overheating.

13. Handpiece according to claim 7, wherein the system for cooling the light guide uses the Peltier effect.

* * * * *

UNITED STATES PATENT AND TRADEMARK OFFICE
CERTIFICATE OF CORRECTION

| | |
|---|---|
| PATENT NO. | : 8,672,987 B2 |
| APPLICATION NO. | : 13/063448 |
| DATED | : March 18, 2014 |
| INVENTOR(S) | : Christophe Hottinger and Pascale Tannous |

Page 1 of 1

It is certified that error appears in the above-identified patent and that said Letters Patent is hereby corrected as shown below:

On the Title Page:

Item (73), change the Assignee from "Dormed" to --Dermeo--.

Signed and Sealed this
Eighth Day of July, 2014

Michelle K. Lee
*Deputy Director of the United States Patent and Trademark Office*